United States Patent
Benedek

(10) Patent No.: US 10,144,664 B2
(45) Date of Patent: *Dec. 4, 2018

(54) ANAEROBIC FERMENTATION TO PRODUCE BIOGAS

(71) Applicant: ANAERGIA INC., Burlington (CA)

(72) Inventor: Andrew Benedek, Rancho Santa Fe, CA (US)

(73) Assignee: Anaergia Inc., Burlington (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/209,259

(22) Filed: Jul. 13, 2016

(65) Prior Publication Data

US 2016/0318787 A1 Nov. 3, 2016

Related U.S. Application Data

(63) Continuation of application No. 13/201,863, filed as application No. PCT/CA2010/000207 on Feb. 18, 2010, now Pat. No. 9,416,372.

(Continued)

(51) Int. Cl.
*C02F 11/04* (2006.01)
*B01D 61/14* (2006.01)
(Continued)

(52) U.S. Cl.
CPC ............ *C02F 11/04* (2013.01); *B01D 61/145* (2013.01); *B01D 61/147* (2013.01); *B01D 61/18* (2013.01);
(Continued)

(58) Field of Classification Search
CPC ...... C02F 11/04; C02F 3/2853; C02F 11/121; C02F 2103/20; C02F 2203/004;
(Continued)

(56) References Cited

U.S. PATENT DOCUMENTS 3,220,945 A 11/1965 Torpey
3,226,317 A 12/1965 Albertson
(Continued)

FOREIGN PATENT DOCUMENTS

CA 2641270 A1 12/2009
CN 201620071 U 11/2010
(Continued)

OTHER PUBLICATIONS

Machine-generated English Translation of DE 102004030482, dated Jul. 25, 2018.*

(Continued)

*Primary Examiner* — Fred Prince

(57) ABSTRACT

A process and apparatus for the anaerobic digestion of organic wastes, preferably to also produce a useful biogas, is described. The waste may have a total solids (TS) concentration of 6% or less while a digester is operated at a higher solids concentration, for example with a feed TS concentration of 8-12%. One or more separation stages downstream of the digester separate active bacteria and undigested organics from the digestate, and return separated matter to the digester. Optionally, a feed thickening apparatus and step may be provided upstream of the digester. The upstream thickener and recycle from the downstream separation stages are operated such that the TS of the combined inputs to the digester is within a desired range.

13 Claims, 2 Drawing Sheets

Related U.S. Application Data

Figure 1:
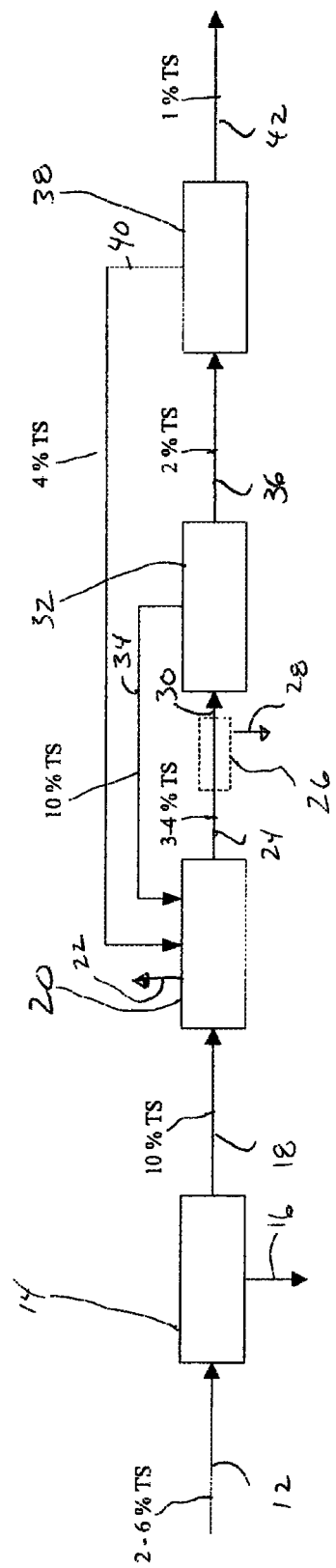

(60) Provisional application No. 61/153,489, filed on Feb. 18, 2009.

(51) Int. Cl.

| | | |
|---|---|---|
| *B01D 61/18* | (2006.01) | |
| *C02F 3/28* | (2006.01) | |
| *C12P 5/02* | (2006.01) | |
| *C02F 11/12* | (2006.01) | |
| *C12M 1/107* | (2006.01) | |
| *C12M 1/26* | (2006.01) | |
| *C02F 103/20* | (2006.01) | |

(52) U.S. Cl.
CPC .......... *C02F 3/2853* (2013.01); *C02F 11/121* (2013.01); *C12M 21/04* (2013.01); *C12M 33/00* (2013.01); *C12P 5/023* (2013.01); *B01D 2311/04* (2013.01); *B01D 2311/25* (2013.01); *B01D 2311/2642* (2013.01); *B01D 2311/2649* (2013.01); *B01D 2315/06* (2013.01); *C02F 2103/20* (2013.01); *C02F 2203/004* (2013.01); *Y02E 50/343* (2013.01)

(58) Field of Classification Search
CPC .... B01D 61/145; B01D 61/147; B01D 61/18; B01D 2311/04; B01D 2311/25; B01D 2311/2642; B01D 2311/2649; B01D 2315/06; C12M 21/04; C12M 33/00; C12P 5/023; Y02E 50/343
USPC ................................ 210/603, 252, 259, 294
See application file for complete search history.

(56) References Cited

U.S. PATENT DOCUMENTS

| | | | |
|---|---|---|---|
| 3,248,323 | A | 4/1966 | Albertson |
| 4,042,493 | A | 8/1977 | Matsch et al. |
| 4,185,680 | A | 1/1980 | Lawson |
| 4,329,428 | A | 5/1982 | Ghosh et al. |
| 4,473,590 | A | 9/1984 | Weigandt et al. |
| 4,626,354 | A | 12/1986 | Hoffman et al. |
| 4,981,593 | A | 1/1991 | Priestley et al. |
| 5,015,384 | A | 5/1991 | Burke |
| 5,723,048 | A | 3/1998 | Kobayashi et al. |
| 5,733,455 | A | 3/1998 | Molof et al. |
| 6,015,496 | A | 1/2000 | Khudenko |
| 6,500,340 | B1* | 12/2002 | Burke ....................... C02F 3/28 210/601 |
| 7,267,774 | B2 | 9/2007 | Peyton et al. |
| 7,396,453 | B1 | 7/2008 | Probst |
| 7,641,796 | B2 | 1/2010 | Stroot et al. |
| 8,012,352 | B1 | 9/2011 | Giraldo et al. |
| 8,197,690 | B2 | 6/2012 | Frechen et al. |
| 9,181,120 | B2 | 11/2015 | Josse et al. |
| 9,416,372 | B2* | 8/2016 | Benedek ............ B01D 61/145 |
| 2002/0170863 | A1 | 11/2002 | Singh et al. |
| 2002/0192809 | A1 | 12/2002 | Lanting et al. |
| 2003/0111411 | A1 | 6/2003 | Lorenz et al. |
| 2005/0016919 | A1 | 1/2005 | Hagino et al. |
| 2005/0040103 | A1 | 2/2005 | Abu-Orf et al. |
| 2005/0194310 | A1 | 9/2005 | Yamamoto et al. |
| 2005/0252858 | A1 | 11/2005 | Peyton et al. |
| 2006/0027495 | A1 | 2/2006 | Hough et al. |
| 2006/0065595 | A1 | 3/2006 | Menke et al. |
| 2003/0266703 | | 11/2006 | Stroot |
| 2006/0249449 | A1 | 11/2006 | Nakhla et al. |
| 2006/0266703 | A1 | 11/2006 | Stroot et al. |
| 2006/0272198 | A1 | 12/2006 | Yoon et al. |
| 2007/0108125 | A1 | 5/2007 | Cho et al. |
| 2007/0209999 | A1 | 9/2007 | Smith et al. |
| 2008/0169245 | A1 | 7/2008 | Roa-Espinosa et al. |
| 2009/0050552 | A1 | 2/2009 | Novak et al. |
| 2009/0186136 | A1 | 7/2009 | Lindeboom et al. |
| 2009/0209025 | A1 | 8/2009 | Goschl et al. |
| 2009/0218280 | A1 | 9/2009 | Josse |
| 2009/0301963 | A1 | 12/2009 | Brockmann et al. |
| 2010/0018917 | A1 | 1/2010 | Fitch et al. |
| 2010/0021979 | A1 | 1/2010 | Facey et al. |
| 2010/0032370 | A1 | 2/2010 | Allen et al. |
| 2010/0089823 | A1 | 4/2010 | Lugowski et al. |
| 2010/0193416 | A1* | 8/2010 | Barbaro .................. C02F 9/00 210/102 |
| 2010/0213121 | A1 | 8/2010 | Miller, III |
| 2011/0203992 | A1 | 8/2011 | Liu et al. |
| 2012/0145627 | A1 | 6/2012 | Benedek et al. |
| 2013/0105390 | A1 | 5/2013 | Gray et al. |
| 2014/0034574 | A1 | 2/2014 | Josse et al. |
| 2014/0131272 | A1 | 5/2014 | Josse |
| 2014/0166555 | A1 | 6/2014 | Dibel et al. |

FOREIGN PATENT DOCUMENTS

| | | |
|---|---|---|
| DE | 1459464 A1 | 2/1969 |
| DE | 4326603 A1 | 2/1995 |
| DE | 4333468 A1 | 4/1995 |
| DE | 102004030482 A1 | 8/2005 |
| DE | 102006034984 A1 | 1/2008 |
| EP | 0646547 A2 | 4/1995 |
| EP | 0737651 A1 | 10/1996 |
| EP | 0605826 B1 | 8/1997 |
| KR | 100872358 B1 | 12/2008 |
| WO | 9942423 A1 | 8/1999 |
| WO | 2010010071 A2 | 1/2010 |
| WO | 2010094115 A1 | 8/2010 |
| WO | 2011002303 A1 | 1/2011 |
| WO | 2012019310 A1 | 2/2012 |
| WO | 2012103629 A1 | 8/2012 |
| WO | 2012109737 A1 | 8/2012 |
| WO | 2014172273 A1 | 10/2014 |

OTHER PUBLICATIONS

An et al., "The Integration of Methanogenesis with Shortcut Nitrification and Denitrification in a Combined UASB with MBR", Bioresource Technology, Jun. 2008, vol. 99 (9), pp. 3714-3720.

Appels et al., "Principles and Potential of the Anaerobic Digestion of Waste-Activated Sludge", Progress in Energy and Combustion Science, Dec. 2008, vol. 34 (6), pp. 755-781.

Brown & Caldwell "Central Kitsap County Wastewater Treatment Plant Alternatives Development Workshop", dated Oct. 28, 2008.

European Patent Application No. 10743360, Office Action dated Sep. 17, 2014.

European Patent Application No. 10743360, Supplementary European Search Report dated Aug. 31, 2012.

European Patent Application No. 10743360, Supplementary European Search Report dated Sep. 18, 2012.

European Patent Application No. EP11815975, Supplementary European Search Report dated Aug. 4, 2016.

European Patent Application No. EP11815975, Supplementary Partial European Search Report dated Jan. 7, 2016.

Fakhru'l-Razi, "Ultrafiltration Membrane Separation for Anaerobic Wastewater Treatment", Water Science and Technology, Dec. 1994, vol. 30 (12), pp. 321-327.

Forster-Carneiro et al., "Influence of Total Solid and Inoculum Performance of Anaerobic Food Waste", Bioresource Technology, Oct. 2008, vol. 99 (15), pp. 6994-7002.

International Patent Application No. PCT/CA2010/000207, International Preliminary Report on Patentability dated Sep. 1, 2011.

International Patent Application No. PCT/CA2010/000207, International Search Report dated Jun. 15, 2010.

International Patent Application No. PCT/CA2011/050498, International Preliminary Report on Patentability dated Feb. 28, 2013.

International Patent Application No. PCT/CA2011/050498, International Search Report and Written Opinion dated Oct. 20, 2011.

International Patent Application No. PCT/CA2011/050726, International Preliminary Report on Patentability dated Aug. 15, 2013.

International Patent Application No. PCT/CA2011/050726, International Search Report dated Mar. 1, 2012.

(56) References Cited

OTHER PUBLICATIONS

International Patent Application No. PCT/CA2016/050060, International Search Report dated Apr. 6, 2016.
International Patent Application No. PCT/US2013/027403, International Search Report dated Oct. 1, 2011.
Korea Ind Tech Inst, English language abstract of KR 100872358, published Dec. 5, 2008, 1 page.
Kummer et al., English language abstract of DE4326603, published Feb. 9, 1995, 1 page.
Parravicini et al., "Aeration of anaerobically digested sewage sludge for COD and nitrogen removal: optimization at large-scale," Water Science and Technology, 2008, vol. 57 (2), pp. 691-698.
King et al., "Microfiltration-Membrane-Coupled Bioreactor for Urban Wastewater Reclamation", Desalination, Dec. 2001, vol. 141 (1), pp. 63-73.
Sieger et al., "White Paper on High Performance Anaerobic Digestion", Jan. 2004, pp. 1-17.
European Application No. 1185757, Supplementary European Search Report dated Jun. 5, 2014, 6 Pages.
International Patent Application No. PCT/CA2010/000207 Written Opinion, dated Jun. 15, 2010, 5 pages.
International Patent Application No. PCT/CA2011/050726 Written Opinion, dated Mar. 1, 2012, 6 pages.
International Patent Application No. PCT/CA2016/050060 Written Opinion, dated Apr. 6, 2016, 6 pages.
European Patent Application No. 10743360, Decision to refuse a European Patent application dated Dec. 16, 2016.
European Patent Application No. 10743360, Minutes of Oral Proceedings dated Dec. 15, 2016.
Canadian Patent Application No. 2,752,747, Office Action dated Jan. 11, 2018.

\* cited by examiner

ANAEROBIC FERMENTATION TO PRODUCE BIOGAS

CROSS REFERENCE TO RELATED APPLICATIONS

This application is continuation of U.S. application Ser. No. 13/201,863, filed Feb. 28, 2012, which is a national phase entry of PCT Application No. PCT/CA2010/000207, filed Feb. 18, 2010, which claims the benefit of U.S. Provisional Application No. 61/153,489, filed Feb. 18, 2009. U.S. patent application Ser. No. 13/201,863, PCT Application PCT/CA2010/000207, and U.S. Provisional Application 61/153,489 are incorporated by reference.

FIELD

This specification relates to a process or apparatus for anaerobic fermentation or digestion of a biomass to produce a biogas.

BACKGROUND

A biogas may be produced through the anaerobic digestion or fermentation of a material containing biomass. The feedstock is typically a waste product, such as manure or sewage. The biogas is typically comprised of 50-75% methane and 25-50% carbon dioxide. Other gases, such as nitrogen, hydrogen, hydrogen sulfide or oxygen may be also present but collectively are unlikely to account for more than 10% of the biogas. Of these other gases, nitrogen is likely to be the largest component. The biogas can be burned directly with oxygen and so is usable as a fuel. The methane within the biogas can also be concentrate to provide a replacement for natural gas.

Biogas can be produced in an anaerobic digester. The digestion process involves microorganisms, primarily bacteria, which break down or convert the input materials to produce the biogas and an effluent. The process involves a series of bacteria types and processes, primarily hydrolysis, acidogenesis, acetogenesis and methanogenesis. The effluent, which may be called digestate, contains residual solid and liquid products. Besides producing useful biogas, the solid component of digestate is reduced in volume and mass compared to the feedstock. Some of the products within the digestate are useful, for example as a fertilizer, but others are waste products or require further processing to produce useful products. Accordingly, the digestate must be separated, and some of its separated components further processed, to produce useful products or safely dispose of it.

The principal component of the digester is a sealed tank, which contains the feed undergoing digestion and the active bacteria. Depending on the species of methanogenic bacteria used, the reactor may be operated at mesophilic (20-45 C, preferably 37-41 C) or thermophilic (50-70 C, preferably 50-52 C) temperatures. The tank may be filled in batches or operated with continuous (including semi-continuous or periodic) feed, digestate and gas removal. The digester may operate in a high solids mode, with a total suspended solids (TSS) concentration of up to 20%, or in a low solids mode with TSS of 15% or less, more often 10% or less. Continuous reactor designs include continuously stirred-tank reactors (CSTR), upflow anaerobic sludge blanket (UASB), expanded granular sludge bed (EGSB) and internal circulation reactors (IC), in single or multiple stages. Operation in low solids mode requires a larger reactor but has some advantages. For example, less energy is required to mix the contents of a low solids mode digester due to reduced viscosity. Further, the effluent from a low solids mode digester may be handled using ordinary pumps whereas high solids mode digestion produces a thick sludge effluent that is difficult to handle.

The composition of the feedstock is important to the biogas generation process. Anaerobic digesters were originally designed primarily for use with cattle manure and sewage. Other feedstock may have a different composition of biodegradable material. In general, simple carbohydrates are easiest to digest whereas large molecules are more difficult to digest. The carbon to nitrogen ratio of the feedstock is also relevant, with a C:N ratio of 20-30:1 being preferred. The moisture content or solids concentration may also vary between feedstocks.

INTRODUCTION

This section is intended to introduce the reader to the more detailed disclosure that follows, and not to limit or define any claimed or disclosed invention. One or more inventions may reside in any combination or sub-combination of apparatus elements or process steps described in this document.

A process and apparatus will be described herein which improves, or at least provides a useful alternative to, the anaerobic digestion of organic wastes to produce a biogas. Although they may also be useful in other applications, the process and apparatus described herein may be used with liquid or liquefied wastes having low solids content, for example with a total solids (TS) concentration of 6% or less, or 4% or less. For example, waste water from a slaughter house or food processing plant may have a TS concentration of 1-2%. Pig manure may have a TS concentration of 2-3%. Despite the low solids content of the feedstock, a digester is operated at a higher feed solids concentration, though still in low solids mode, for example with a feed TS concentration of 8-12% or 8-10%.

The apparatus and process uses one or more separation stages downstream of the digester to separate active bacteria and undigested organics from the digestate, and return separated matter to the digester. Multiple sequential separation stages may be provided with the retained particle size decreasing in the downstream direction. Preferably, one of the stages comprises a membrane filtration unit. Optionally, a feed thickening apparatus and step may be provided upstream of the digester.

The optionally thickened feed and one or more recycle streams are inputs to the digester. The combined input solids concentration, meaning the solids concentration of a mixture of the inputs or a volumetric flow rate weighted average of the solids concentrations of the individual inputs, is within a range desired or pre-selected for operation of the digester. A recycle stream, particularly a recycle stream from a membrane filtration unit, may have a solids concentration below the desired digester operation range. A second recycle stream or upstream thickening or both may be used to raise the combined input solids concentration to within the desired digester operation range.

The process and apparatus can provide useful advantages. Without limitation, low solids feeds may be digested more efficiently at a higher, but not overly high, controlled solids concentration in the digester. Bacteria and undigested biomass may be retained in the digester for a longer effective residence time, without increasing the hydraulic residence time of the digester tank. The effluent is separated into two or more streams, which may reduce post-processing requirements before the effluent can be reused or safely disposed.

DRAWINGS

Figure 2:
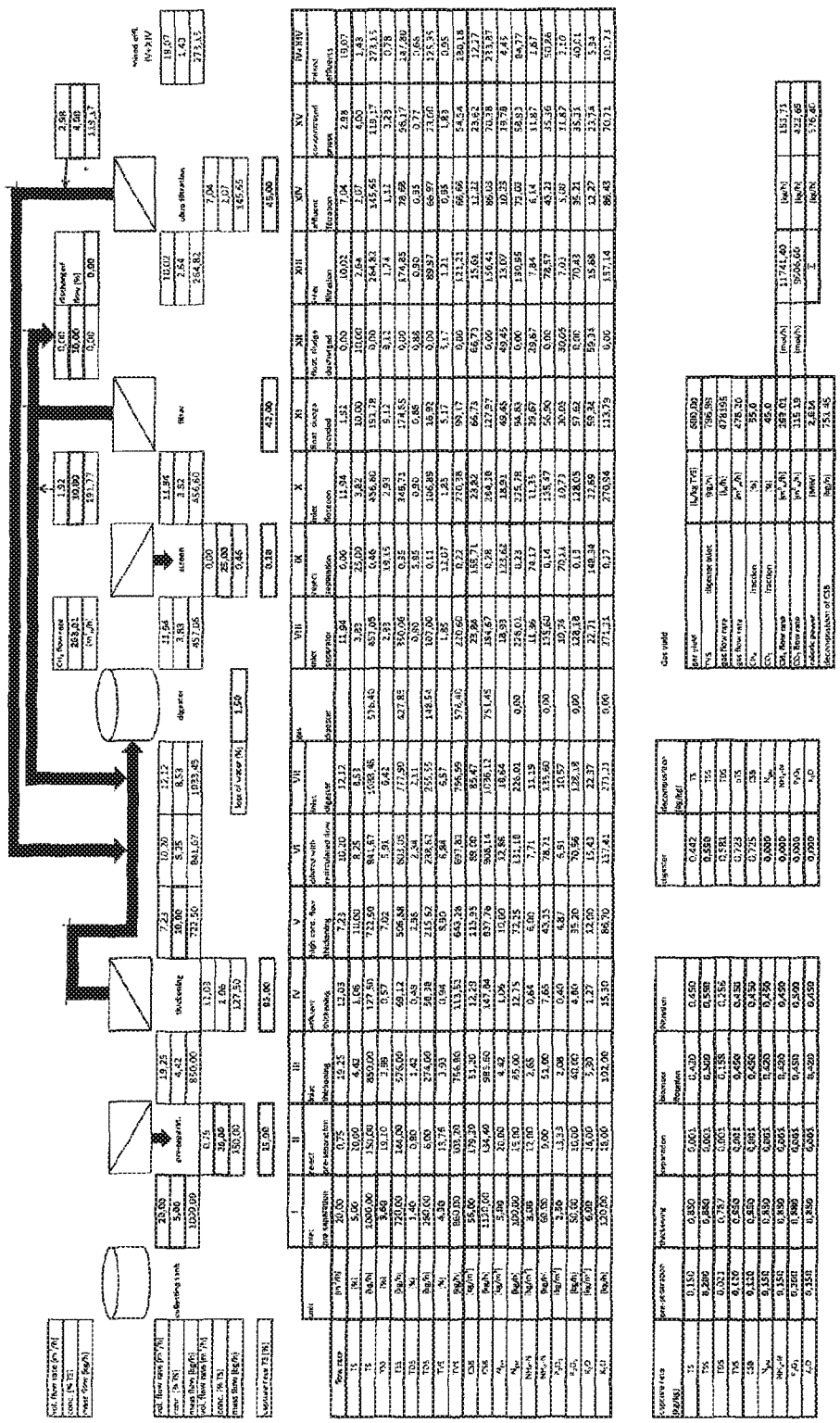

FIG. 1 is a flow sheet of a digestion process.
FIG. 2 is a mass balance of an example of a digestion process.

DESCRIPTION OF VARIOUS EMBODIMENTS

FIG. 1 shows a plant 10 for treating a feed liquid 12 containing organic matter. The feed liquid 12 may have a low solids content, for example a total solids (TS) concentration of 6% or less. Solids content may also be measured by other parameters, for example as total suspended solids (TSS) concentration, with suitable adjustment of the numerical values. The feed liquid 12 may be a waste stream, such as waste water from a slaughter house or food processing plant or pig manure. The feed liquid 12 may be pre-separated to remove contaminants such as plastic, glass or metals or un-digestible solids.

The feed liquid 12 optionally flows into a first thickener 14. The first thickener 14 is a solid—liquid separation device such as a clarifier, sedimentation basin, flotation device or filter, or a combination of one or more of these or other devices. The first thickener 14 produces a first thickener effluent 16. The first thickener effluent 16 is primarily water, with a TS concentration typically of 2% or less, that may be treated for example as municipal waste water. The first thickener 14 also produces, as a retained portion, a thickened feed liquid 18. The thickened feed liquid 18 may have a TS concentration of, for example, 10% or more. The TS concentration of the thickened feed liquid 18 may be higher than a minimum pre-determined or design TS feed concentration for digestion, and possible at or above the upper limit of a desired digester operation range.

The thickened feed liquid 18 flows into a digester 20. The digester 20 comprises one or more tanks, in series or parallel or both, with mixing or other apparatus as is known for use in batch or continuous processes in the field of anaerobic digestion. For example, the digester 20 may be a sealed tank with an internal mechanical mixer. A suitable digester 20 is available from UTS Biogastechnik BmbH as sold under the Helios trade-mark. The digester 20 contains microorganisms, primarily bacteria, to digest the thickened feed liquid 18. The digester 20 may be seeded with the microorganisms, or the microorganisms may be carried into the digester 20 as a component of the thickened feed liquid. The microorganisms convert solids in the thickened feed liquid 18 into, among other things, a biogas 22 which is collected and removed from the digester 20.

The digester 20 also produces a digestate 24. Due to the action of the microorganisms in the digester 20, the digestate 24 has a reduced TS concentration relative to the thickened feed liquid 18, for example 3-4%. Optionally, the digestate 24 can pass through a separator 26 as a first of a plurality of downstream separation stages. The separator 26 provides a coarse separation, for example as produced by a static screen, vibrating screen, screw press or similar equipment. A portion of the separated solids 28 from the separator 26 may be returned to the digester, but preferably the separated solids 28 are removed from the plant 10. The separated solids 28 are likely to have high concentrations of materials that are difficult for anaerobic bacteria to digest but may be further processed to produce useful products such as fertilizer or building materials.

Separator effluent 30 flows to a second thickener 32. The second thickener 32 has a smaller separation size than the separator 26. For example, the second thickener 32 may be a filter with a screen or mesh having an opening size in the range of about 10-200 microns. For example, the second thickener 32 may be a drum filter, disc filter or similar equipment. The second thickener 32 produces a sludge 34 with an elevated solids content, for example a TS concentration of 10% or more. The TS concentration of the sludge 34 may be higher than a minimum pre-determined or design TS feed concentration for digestion, and possible at or above the upper limit of a desired digester operation range. A significant portion, for example 50% or more up to 100%, of the sludge 34 is preferably recycled to the digester 20.

The second thickener 32 also produces a filtrate 36 with a reduced solids concentration, for example with a TS concentration of about 2%. The filtrate 36 flows to a membrane filtration unit 38. The membrane filtration unit 38 may have a pore size in the microfiltration range or smaller. The membrane filtration unit 38 may include one or more pressure fed cross flow filtration modules with tubular or hollow fiber membranes. To prevent oxygenation of the filtrate 36, the membranes may be cleaned by backpulsing, relaxation, temporary increases in flow velocity or bubbling with a gas not containing significant amounts of oxygen. Alternatively, the membrane filtration unit may include one or more immersed suction driven membrane modules of flat sheet or hollow fiber membranes. In this case, cleaning may be performed scouring bubbles of a gas not containing significant amounts of oxygen. The gas may comprise one or more inert gases, or gases produced by anaerobic digestion such as biogas or any of its components such as methane, carbon dioxide, or nitrogen. For example, waste gases left after enriching the biogas 22, primarily carbon dioxide, may be used for bubble scouring in the membrane filtration unit 38. Preferably, the membrane modules are operated in a sealed tank with gases used for scouring bubbles captured in a head space of the tank and recycled to the aerators, in a manner similar to the gas recycle in European Patent EP 0 605 826 B1 or US Patent Application Publication No. US 2002/0170863, both of which are incorporated herein in their entirety by this reference to them.

The membrane filtration unit 38 produces a retentate 40 with an elevated solids content and a permeate 42 with a reduced solids content. The permeate 40 may have a TS concentration of about 1% and may be suitable, optionally with further treatment, even for discharge into the environment or into a water reclamation process. The solids content of the retentate 40 may be less than a desired digester operation range. A significant portion, for example 50% or more up to 100%, of the retentate 40 is preferably recycled to the digester 20.

The recycle of retentate 40 and sludge 34 to the digester 20 increases the organic and sludge load of the digester 20. Recycle of the retentate 40 is particularly desirable since it drastically reduces the loss of useful, live microorganisms. The recycle of sludge 34 increases the solids content of the combined inputs (feed and recycle) to the digester 20. It is not desirable to increase the solids content of the combined inputs to the digester beyond a pre-determined or design feed solids concentration for digestion. However, significant or full recycle of the retentate 40 tends to dilute the combined inputs to the digester 20. Recycling the sludge 34 and use of the thickener 14, or both, may be used to counter dilution by recycled retentate 40 and provide a combined input solids concentration within the desired digester operation range. The combined input solids concentration, measured as TS concentration, may be in the range of 8 12% or 8-10%.

EXAMPLES

FIG. 2 shows a design example of an anaerobic digestion process with pre-separation, pre-thickening, digestion, screening separation, filtration and membrane ultrafiltration. Flow rates and concentrations before and after these steps are shown in the Figure.

I claim:

1. A process for the treatment of a liquid comprising organic material, the process comprising steps of, anaerobic digestion of the liquid to produce a digestate; and separating solids from the digestate in two or more sequential separation steps wherein an upstream one of the two or more sequential separation steps comprises separating particles above a first size and a downstream one of the two or more sequential separation steps comprises separating particles above a second size that is smaller than the first size, wherein an amount of separated matter from each separation step that is recycled to the digester, expressed as a percentage of the total amount of separated matter, increases or is constant in the downstream direction between adjacent separation steps.

2. The process of claim 1 wherein separated solids removed from the upstream one of the separation steps are not recycled to the digester.

3. The process of claim 1 wherein a recycle stream from the downstream one of the separation steps has a solids concentration greater than a combined input solids concentration for the anaerobic digestion step.

4. The process of claim 1 further comprising a step of membrane separation downstream of the downstream one of the separation steps, wherein solids separated in the membrane separation step are recycled to the digester.

5. The process of claim 1 further comprising a step of thickening the liquid upstream of the digester.

6. The process of claim 1 wherein the upstream one of the separation steps comprises separation by one of a static screen, a vibrating screen, and a screw press.

7. A process for the treatment of a liquid comprising organic material, the process comprising steps of, anaerobic digestion of the liquid in a digester to produce a digestate; separating solids from the digestate in two or more sequential separation steps comprising a membrane separation step; and, recycling separated matter from two or more of the separation steps to the digester in two or more recycle streams wherein one of the one or more recycle streams has a total solids concentration that is above the total solids concentration of the liquid in the digester and the recycle stream from the membrane separation step has a total solids concentration that is less than the total solids concentration of the liquid in the digester.

8. The process of claim 7 further comprising a step of thickening the liquid prior to anaerobic digestion of the liquid.

9. The process of claim 8 wherein the extent of thickening of the liquid is selected so as to produce, in combination with the flow rate and solids concentration of the two or more recycle streams, a combined input solids concentration to the digester that is within a predetermined operating range.

10. The process of claim 8 wherein the thickened liquid has a TS concentration that is higher than the TS concentration of a flow rate weighted average of the TS concentrations of the thickened liquid and recycle steams.

11. The process of claim 7 wherein the liquid has a TS concentration of 6% or less.

12. The process of claim 11 wherein the digester is operated as a mixed reactor with feed, including any recirculated streams, at a combined input solids concentration of 8-12%.

13. The process of claim 7 wherein two or more post-digester effluent streams are produced.

* * * * *